(12) United States Patent
Gaster et al.

(10) Patent No.: US 6,391,891 B1
(45) Date of Patent: May 21, 2002

(54) BICYCLIC COMPOUNDS AS LIGANDS FOR 5-HT$_1$ RECEPTORS

(75) Inventors: Laramie Mary Gaster, Bishop's Stortford; Paul Adrian Wyman, Epping; Sean Thomas Flynn, St Albans, all of (GB)

(73) Assignee: SmithKline Beecham plc (GB)

( * ) Notice: Subject to any disclaimer, the term of this patent is extended or adjusted under 35 U.S.C. 154(b) by 0 days.

(21) Appl. No.: 09/463,704

(22) PCT Filed: Aug. 6, 1998

(86) PCT No.: PCT/EP98/05116

§ 371 Date: Jan. 26, 2000

§ 102(e) Date: Jan. 26, 2000

(87) PCT Pub. No.: WO99/07700

PCT Pub. Date: Feb. 18, 1999

(30) Foreign Application Priority Data

Aug. 9, 1997 (GB) .............................. 9716804
Jan. 26, 1998 (GB) .............................. 9801633

(51) Int. Cl.$^7$ ..................... A61K 31/445; C07D 401/14
(52) U.S. Cl. ................. 514/318; 514/316; 514/323; 514/329; 546/187; 546/193; 546/201; 546/202; 546/205
(58) Field of Search ................ 514/316, 318, 514/323, 339; 546/187, 193, 201, 202, 205

(56) References Cited

U.S. PATENT DOCUMENTS 5,708,008 A * 1/1998 Audia et al. ............... 514/323

FOREIGN PATENT DOCUMENTS

| EP | 0 533 266 A1 | 3/1993 |
|---|---|---|
| EP | 0 533 267 A1 | 3/1993 |
| EP | 0 533 268 A1 | 3/1993 |
| EP | 0 581 538 A1 | 2/1994 |
| EP | 0 733 628 A1 | 9/1996 |
| EP | 0 812 826 A1 | 12/1997 |
| GB | 2 289 465 | 11/1995 |
| WO | WO 93/11106 | 6/1993 |
| WO | WO 94/24127 | 10/1994 |
| WO | WO 95/06044 | 3/1995 |
| WO | WO 95/06636 | 3/1995 |
| WO | WO 95/28400 | 10/1995 |
| WO | WO 95/32196 | 11/1995 |

* cited by examiner

*Primary Examiner*—Ceila Chang
(74) *Attorney, Agent, or Firm*—James M. Kanagy; Charles M. Kinzig

(57) ABSTRACT

The invention relates to compounds which are ligands for 5HT1, of formula (I)

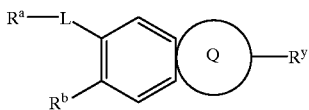

(I)

Wherein L, Q, R$^a$, R$^b$ and R$^y$ are as defined in the specification, processes for their preparation and their pharmaceutical composition as well as their use in the treatment of anxiety and depression.

6 Claims, No Drawings

BICYCLIC COMPOUNDS AS LIGANDS FOR 5-HT$_1$ RECEPTORS

This application is a 371 of PCT/EP98/05116 filed Aug. 6, 1998.

The present invention relates to novel compounds, processes for their preparation, and pharmaceutical compositions containing them.

EPA 0733628 discloses a series of indole derivatives which are said to possess 5HT$_{1F}$ agonist activity. These compounds are alleged to be of use in the treatment of migraine and associated disorders. EPA 0533266/7/8 disclose a series of benzanilide derivatives which are said to possess 5-HT$_{1D}$ receptor antagonist activity. The 5-HT$_{1D}$ receptor was subsequently found to consist of a pair of gene products originally designated 5-HT$_{1D\alpha}$ and 5-HT$_{1D\beta}$ receptors which have more recently been reclassified as 5-HT$_{1D}$ and 5-HT$_{1B}$ receptors, respectively. (Hartig, P. R. et al., Trends in Pharmacological Sciences 1992, Vol. 13, page 152, Hartig, P. R. et al., Trends in Pharmacological Sciences, 1996, Vol. 17, page 103).

A structurally distinct class of compounds have now been found that are ligands for 5HT$_{1A}$, 5HT$_{1B}$ and 5HT$_{1D}$ receptors. It is expected that such compounds will be useful for the treatment and prophylaxis of various disorders. In a first aspect, the present invention therefore provides a compound of formula (I) or a salt thereof:

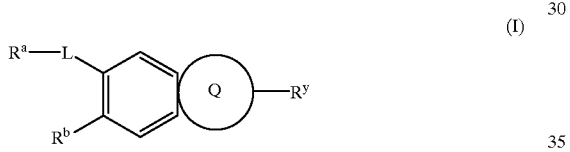

(I)

in which R$^a$ is a group of formula (i)

(i)

in which P$^1$ is phenyl, bicyclic aryl, a 5 to 7 membered heterocyclic ring containing 1 to 3 heteroatoms selected from oxygen, nitrogen and sulphur, or a bicyclic heterocyclic ring containing 1 to 3 heteroatoms selected from oxygen, nitrogen and sulphur; R$^1$ is hydrogen, halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, hydroxyC$_{1-6}$alkoxy, C$_{1-6}$alkoxyC$_{1-6}$alkoxy, nitro, trifluoromethyl, cyano, SR$^9$, SOR$^9$, SO$_2$R$^9$, SO$_2$NR$^{10}$R$^{11}$, CO$_2$R$^{10}$, CONR$^{10}$R$^{11}$, CONR$^{10}$(CH$_2$)$_c$CO$_2$R$^{11}$, (CH$_2$)$_c$NR$^{10}$R$^{11}$, (CH$_2$)$_c$CONR$^{10}$R$^{11}$, (CH$_2$)$_c$NR$^{10}$COR$^{11}$, (CH$_2$)$_c$CO$_2$C$_{1-6}$alkyl, CO$_2$(CH$_2$)$_c$OR$^{10}$, NR$^{10}$R$^{11}$, NR$^{10}$CO$_2$R$^{11}$, NR$^{10}$CONR$^{10}$R$^{11}$, CR$^{10}$=NOR$^{11}$ where R$^9$ is C$_{1-6}$alkyl, R$^{10}$ and R$^{11}$ are independently hydrogen or C$_{1-6}$alkyl and c is 1 to 4;

R$^2$ is hydrogen, halogen, C$_{1-6}$alkyl, C$_{3-6}$cycloalkyl, C$_{3-6}$cycloalkenyl, C$_{1-6}$alkoxy, COC$_{1-6}$alkyl, aryl, acyloxy, hydroxy, nitro, trifluoromethyl, cyano, CO$_2$R$^{10}$, CONR$^{10}$R$^{11}$, NR$^{10}$R$^{11}$ where R$^{10}$ and R$^{11}$ are as defined in R$^1$;

a is 1, 2 or 3;

or R$^a$ is a group of formula (ii)

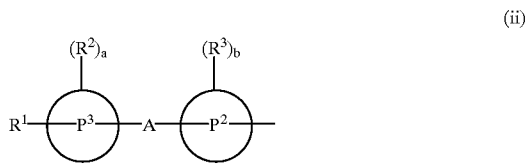

(ii)

wherein
p$^2$ and p3 are independently phenyl, bicyclic aryl, a 5- to 7- membered heterocyclic ring containing 1 to 3 heteroatoms selected from oxygen, nitrogen and sulphur, or a bicyclic heterocyclic group containing 1 to 3 heteroatoms selected from oxygen, nitrogen or sulphur;

A is a bond or oxygen, S(O)$_m$ where m is 0, 1 or 2, carbonyl, or CH$_2$ or NR$^4$ where R$^4$ is hydrogen or C$_{1-6}$alkyl;

R$^1$ is as defined above for formula (i) or is a 5 to 7-membered heterocyclic ring, containing 1 to 3 heteroatoms selected from oxygen, nitrogen or sulphur, optionally substituted by C$_{1-6}$alkyl, halogen or C$_{1-6}$alkanoyl;

R$^2$ and R$^3$ are as defined for R$^2$ in formula (i);
and a and b are independently 1, 2 or 3;

L is a group of formula

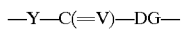
—Y—C(=V)—DG— in which
Y is —NH—, NR$^5$ where R$^5$ is C$_{1-6}$alkyl, or Y is —CH$_2$— or —O—,
V is oxygen or sulphur;
D is nitrogen, carbon or a CH group, G is hydrogen or C$_{1-6}$alkyl, providing that D is nitrogen or a CH group, or G together with R$^b$ forms a group W where W is (CR$^{16}$R$^{17}$)$_t$ where t is 2, 3 or 4 and R$^{16}$ and R$^{17}$ are independently hydrogen or C$_{1-6}$alkyl or W is (CR$^{16}$R$^{17}$)$_u$—J where u is 0, 1, 2 or 3 and J is oxygen, sulphur, CR$^{16}$=CR$^{17}$, CR$^{16}$=N, =CR$^{16}$O, =CR$^{16}$S or =CR$^{16}$—NR$^{17}$ provided that u is not 0 when J is oxygen or sulphur; subject to the proviso that when D is nitrogen, G is hydrogen or C$_{1-6}$alkyl, Q is selected such that together with the phenyl ring to which it is attached it forms an indole ring and further that when:
(a) Y is —NH— or —NR$^5$— and V is oxygen or sulphur; or
(b) both Y and V are oxygen; or
(c) Y is CH$_2$ and V is oxygen
then p$^1$ is not phenyl within the definition of R$^a$ formula (i) and
R$^a$ is not an unsubstituted biphenyl within the definition of formula (ii)
Q is an optionally substituted 5- to 7-membered carbocyclic or heterocyclic ring containing 1 to 3 heteroatoms selected from oxygen, nitrogen or sulphur;
R$^Y$ is a 5- to 7-membered heterocyclic ring containing 1 to 3 heteroatoms selected from oxygen, nitrogen and sulphur;
R$^b$ is hydrogen, halogen, hydroxy, C$_{1-6}$alkyl, trifluoromethyl, C$_{1-6}$alkoxy or aryl; or R$^b$ together with G forms a group W as defined above;

C$_{1-6}$alkyl groups whether alone or as part of another group may be straight chain or branched. The term 'acyloxy' is used herein to describe a group —OC(O)$C_{1-6}$alkyl. The term 'aryl' is used herein to describe, unless otherwise stated, a group such as phenyl. The term 'aralkyl' is used herein to describe, unless otherwise stated, a group such as benzyl.

The bicyclic aryl group represented by $p^1$, $p^2$ and/or $p^3$, which may be partially saturated, is preferably naphthyl.

Examples of bicyclic heterocyclic rings containing 1 to 3 heteroatoms selected from oxygen, nitrogen and sulphur include quinoline, isoquinoline, indole, benzofuran and benzothiophene rings. The heterocyclic groups can be linked to the remainder of the molecule via a carbon atom or, when present, a suitable nitrogen atom.

Examples of 5 to 7 membered heterocyclic rings containing 1 to 3 heteroatoms selected from oxygen, nitrogen and sulphur represented by $p^1$, $p^2$ and/or $p^3$, include thienyl, furyl, pyrrolyl, triazolyl, imidazolyl, oxazolyl, thiazolyl, oxadiazolyl, isothiazolyl, isoxazolyl, thiadiazolyl, pyrimidyl and pyrazinyl, preferably pyridyl.

$R^1$ is preferably a halogen atom for example, fluorine, chlorine or bromine, and $R^2$ and/or $R^3$ are each preferably hydrogen, halogen for example a chloro group or a $C_{1-6}$alkyl group for example a methyl group.

a and b are each preferably 1 or 2.

Within the definition of $R^a$ formula (ii), A is preferably a bond.

In the group L, as defined above:

Y is preferably —NH—.

V is preferably oxygen.

D is preferably nitrogen and G is preferably a hydrogen atom or together with $R^b$ forms group W, preferably —(CH$_2$)$_2$—.

$R^b$ is preferably hydrogen or $R^b$ together with G forms group W referred to above.

Suitably Q is an optionally substituted 5 to 7-membered heterocyclic ring containing 1 to 3 heteroatoms selected from oxygen, nitrogen or sulphur. Preferably Q is a 5- or 6-membered ring containing one or two heteroatoms. Preferably Q, together with the phenyl group to which it attached, forms an indole, indoline, benzoxazole, benzopyran, benzothiophene or benzoxazine ring. Suitable optional substituents for the ring Q include groups $R^1$ and $R^2$ as defined above, preferably $C_{1-6}$alkyl, most preferably methyl.

The group $R^Y$ can be fully or partially saturated and can be linked to the group Q via a carbon atom or, when present, a suitable nitrogen atom. Preferably $R^Y$ is 5 or 6 membered heterocyclic containing 1 or 2 nitrogen atoms. Most preferably $R^Y$ is a piperidinyl group.

Particularly preferred compounds according to the invention include:

N-[3-(1-Methylpiperidin-4-yl)indol-5-yl]-N-[4-(pyridin-4-yl)naphth-1-yl]-urea,

N-[3-(1-Methylpiperidin-4-yl)indol-5-yl]-N'-[3-methyl-4-(pyridin-4-yl)phenyl]-urea, N-[2,3-Dichloro-4-(pyridin-4-yl)phenyl]-N'-[3-(-methylpiperidin-4-yl)indol-5-yl]-urea, N-[2-Chloro-4-(pyridin-4-yl)phenyl]-N'-[3-(1-methylpiperidin-4-yl)indol-5-yl]-urea N-[3-(1-Methylpiperidin-4-yl)indol-5-yl]-4-(pyridin-4-yl)naphth-1-ylacetamide, N-[2,3-Dichlorophenyl]-N'-[7-(1-methylpiperidin-4-yl)-1,2,3,5-tetrahydropyrrolo[2,3-f]indol-1-yl]-urea, N-[7-(1-Methylpiperidin-4-yl)-1,2,3,5-tetrahydropyrrolo[2,3f]indol-1-yl]-N'-[4-(pyridin-4-yl)naphth-1-yl]-urea, N-[3-Chloro-4-(pyridin-4-yl)phenyl]-N'-[3-(1-methylpiperidin-4-yl)indol-5-yl]-urea, N-[3-Chloro-4-(pyridin-4-yl)phenyl]-N'-[3-(1-methyl-1,2,5,6-tetrahydropyridin-4-yl)benzo[b]thiophen-5-yl]-urea, N-[3-(1-Methyl-1,2,5,6-tetrahydropyridin-4-yl)benzo[b]thiophen-5-yl]-N'-[4-(pyridin-4-yl)naphth-1-yl]-urea, N-[3-Chloro-4-(pyridin-4-yl)phenyl]-N'-[3-(1-methylpiperidin-4-yl)benzo[b]thiophen-5-yl]-urea, N-[3-(1-Methylpiperidin-4-yl)benzol[b]thiophen-5-yl]-N'-[4-(pyridin-4-yl)naphth-1-yl]-urea or pharmaceutically acceptable salts thereof Preferred salts of the compounds of formula (I) are pharmaceutically acceptable salts. These include acid addition salts such as hydrochlorides, hydrobromides, phosphates, acetates, fumarates, maleates, tartrates, citrates, oxalates, methanesulphonates and p-toluenesulphonates.

Certain compounds of formula (a) are capable of existing in stereoisomeric forms. It will be understood that the invention encompasses all geometric and optical isomers of the compounds of formula (I) and the mixtures thereof including racemates.

Compounds of the invention can be prepared using procedures known in the art. In a further aspect the present invention provides a process for the preparation of a compound of formula (I) or a pharmaceutically acceptable salt thereof which comprises:

(a) where D is nitrogen and Y is NH, coupling a compound of formula (II):

$$R^a\text{—}N\!=\!C(\!=\!V) \quad\quad\quad (II)$$

in which $R^a$ and V are as defined in formula (I) or a protected derivative thereof with a compound of formula (III).

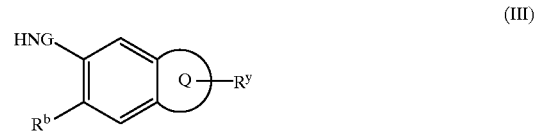

(III)

in which $R^b$, $R^Y$, G, and Q are as defined in formula (I), or a protected derivative thereof; or (b) where D is nitrogen and Y is NH or $NR^5$, reacting a compound of formula (IV)

$$R^a\text{—}NH_2 \text{ or } R^a\text{—}NR^5H \quad\quad\quad (IV)$$

in which $R^a$ and $R^5$ are as defined in formula (I) with a compound of formula (III) together with an appropriate urea forming agent;

(c) where D is nitrogen, reacting a compound of formula (V)

$$R^a\text{—}Y\text{—}(C\!=\!O)\text{—}L^2 \quad\quad\quad (V)$$

in which $R^a$ is as defined in formula (I),

Y is —CH$_2$— or —O— and $L^2$ is an appropriate leaving group, with a compound of formula (III)

(d) where D is carbon or CH, reacting a compound of formula (VI)

$$R^a\text{—}NH_2 \quad\quad\quad (VI)$$

in which $R^a$ is as defined in formula (I) with a compound of formula (VII)

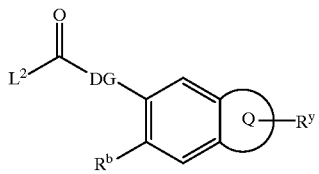

(III)

in which D is carbon or CH, $R^b$, $R^Y$, G, and Q are as defined in formula (I) and $L^2$ is an appropriate leaving group and optionally thereafter:
removing any protecting groups,
converting a compound of formula (I) into another compound of formula (I),
forming a pharmaceutically acceptable salt.

The reaction in process (a) is conveniently effected in an organic solvent such as dichloromethane.

In process (b) the urea forming agent can be carbonyl demidazole, triphosgene or phosgene, and carried out in an inert organic solvent such as dimethylformamide, tetrahydrofuran or dichloromethane at ambient or elevated temperature in the presence of a base such as triethylamine or pyridine.

In process (c) the leaving group $L^2$ may be a halogen e.g. chloro group and the reaction may be carried out in an inert organic solvent such as tetrahydrofuran or dichloromethane at ambient or elevated temperature in the presence of a base such as triethylamine or pyridine.

In process (d) the leaving group $L^2$ may be a halogen e.g. chloro group and the reaction may be carried out in an inert organic solvent such as tetrahydrofuran or dichloromethane at ambient or elevated temperature in the presence of a base such as triethylamine or pyridine.

Compounds of formula (I) can be converted into further compounds of formula (I) using standard techniques.

Intermediate compounds of formula (II), (III), (IV), (V), (VI) and (VII) can be prepared using standard procedures known in the art.

It will be appreciated to those skilled in the art that it may be necessary to protect certain reactive substituents during some of the above procedures. Standard protection and deprotection techniques can be used. For example, primary amines can be protected as phthalimide, benzyl, benzyloxycarbonyl or trityl derivatives. These groups can be removed by conventional procedures well known in the art.

Carboxylic acid groups can be protected as esters. Aldehyde or ketone groups can be protected as acetals, ketals, thioacetals or thioketals. Deprotection is achieved using standard conditions.

The involvement of serotonin receptors in a number of pharmacological effects has been reviewed by R. A. Glennon in "Serotonin Receptors: Clinical Implications", Neuroscience and Behavioural Reviews, 1990, 14, 35 and by L. O. Wilkinson and C. T. Dourish in "Serotonin Receptor Subtypes: Basic and Clinical Aspects" S. Peroutka Ed., John Wiley and Sons, New York, 1991 p.147.

Serotonin (5-hydroxytryptamine; 5HT) receptors have been implicated in a number of pharmacological effects including mood disorders including depression, seasonal affective disorder and dysthymia, anxiety disorders, including generalised anxiety, panic disorder, agoraphobia, social phobia, obsessive compulsive disorder and post-traumatic stress disorder; memory disorders, including dementia, amnesic disorders and age-associated memory impairment; disorders of eating behaviours, including anorexia nervosa and bulimia nervosa, sleep disorders (including disturbances of Circadian rhythm), motor disorders such as Parkinson's disease, dementia in Parkinson's disease, neuroleptic-induced Parkinsonism and tardive dyskinesias, as well as other psychiatric disorders. Serotonin receptor ligands have been shown to be of use in the treatment of emesis and nausea and may also be of use in endocrine disorders such as hyperlactinaemia, vasospasm (particularly in the cerebral vasculature), cerebellar ataxia and hypertension, as well as disorders of the gastrointestinal tract where changes in motility and secretion are involved. They may also be of use in the treatment of sexual dysfunction and hypothermia.

Ligands with high affinity for the $5HT_1$ receptors are well recognised as having therapeutic utility for the treatment of the above conditions. For example: WO 95/31988 refers to the use of a $5\text{-}HT_{1D}$ receptor antagonist in conjunction with a $5\text{-}HT_{1A}$ receptor antagonist to- treat CNS, endocrine and GI disorders; K. Rasmussen (Annual Reports in Medicinal Chemistry, (1995) 30, 1) describes the utility of $5\text{-}HT_{1A}$ receptor agonists and partial agonists in the treatment of various CNS disorders; P. Trouillas (Progress in Brain Research, C. I. de Zeeuw, P. Stara and J. Voogd, Eds. 1997, 144, 589) and G. Maura (J. Neurochemistry, 1996, 66, 202) propose that administration of agonist ligands selective for the $5\text{-}HT_{1A}$ receptor or for both $5\text{-}HT_{1A}$ and $5\text{-}HT_{1D}$ receptors should provide effective treatment for human cerebellar ataxias.

The present invention also provides a compound of general formula (I) or a physiologically acceptable salt or solvate thereof for use in the treatment of the aforementioned disorders.

In a further aspect the invention provides a method of treating the aforementioned disorders which comprises administering an effective amount to a patient in need of such treatment of a compound of general formula (I) or a pharmaceutically acceptable salt or solvate thereof.

In particular the invention provides a compound of general formula (I) or a physiologically acceptable salt or solvate thereof for use in the treatment or prophylaxis of depression.

The affinities of the compounds of this invention for the $5HT_{1A}$, $5\text{-}HT_{1B}$ and $5\text{-}HT_{1D}$ receptors can be determined by the following radioligand binding assay. HEK 293 cells expressing $5\text{-}HT_{1A}$ receptors ($4\times10^7$/ml) are homogenised in Tris buffer and stored in 1 ml aliquots. CHO cells expressing $5\text{-}HT_{1B}$ receptors ($4\times10^7$ cells/ml) are homogenised in Tris buffer and stored in 1.5 ml aliquots. CHO cells expressing $5\text{-}HT_{1D}$ receptors ($0.563\times10^8$/ml) are homogenised in Tris buffer and stored in 1 ml aliquots. 0.4 ml of a cell suspension is incubated with [$^3$H]-5-HT (4 nM) for $5\text{-}HT_{1B/1D}$ receptors and [$^3$H]-8-OH DPAT (1 nM) for $5\text{-}HT_{1A}$ receptors in Tris Mg HCl buffer (pH 7.7) and test drug, at 37° C. for 45 minutes. Each test drug is tested at 10 concentrations (0.01 mM to 0.3 nM final concentration), with non-specific binding defined using 0.01 mM 5-HT. The total assay volume is 0.5 ml. Incubation is stopped by rapid filtration using a Packard Filtermate (filters pre-soaked in 0.3% polyethylenimine) and radioactivity measured by Topcount scintillation counting. pKi values are calculated from the $IC_{50}$ generated by an iterative least squares curve fitting programme.

The intrinsic activity of the compounds of this invention can be determined according to the following procedure. HEK293 cell membranes stably expressing human $5\text{-}HT_{1A}$ receptors and CHO cell membranes stably expressing human 5-HT$_{1B}$ receptors are homogenised in HEPES/EDTA buffer and stored in 1 ml aliquots, and [$^{35}$S]GTPγS binding studies are carried out essentially as described by Lazareno et al., (Life Sci., 1993, 52, 449) with some minor modifications. Membranes from 10$^6$ cells are pre-incubated at 30° C. for 30 minutes in 20 mM HEPES buffer (pH 7.4) in the presence of MgCl$_2$ (3 mM), NaCl (100 mM), GDP (10 μM) and ascorbate (0.2 mM), with or without test compounds. The reaction is started by the addition of 10 μl of [$^{35}$S] GTPγS (100 pM, assay concentration) followed by a further 30 minutes incubation at 30° C. Non-specific binding is determined using nonradiolabelled GTPγS (20 μM) added prior to the membranes. The reaction is terminated by rapid filtration through Whatman GF/B grade filters followed by 5×1 ml washes with ice cold HEPES (20 mM)/MgCl$_2$ (3 mM) buffer. Radioactivity is measured using liquid scintillation spectrometry. This procedure is hereafter referred to as the [$^{35}$S]GTPγS functional assay.

The compounds of formula (I) show high affinity for the 5HT$_{1A}$, 5-HT$_{1B}$ and 5-HT$_{1D}$ receptors. It has been found, using the [$^{35}$S]GTPγS functional assay, that certain compounds of formula (I) appear to be antagonists whilst others appear to be agonists, partial agonists or inverse agonists. The difficulties in describing intrinsic activity of drugs acting at G protein coupled receptors is recognised in the art (Hoyer and Boddeke, Trends in Pharmocological Sciences, July 1993, [Vol. 14], page 270–275). We believe that however these ligands are classified according to this functional assay, the compounds of this invention will be useful antidepressants in vivo.

It will be appreciated by those skilled in the art that the compounds according to the invention may advantageously be used in conjunction with one or more other therapeutic agents, for instance, a selective serotonin reuptake inhibitor (SSRI) antidepressant.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents The tablets may be coated according to methods well known in normal pharmaceutical practice.

Oral liquid preparations may be in the form of, for example, aqueous or oily suspensions, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following Examples illustrate the preparation of compounds of the invention.

DESCRIPTION 1

3-(1-Methyl-1,2,5,6-tetrahydropyridin-4-yl)-5-nitro-1H-indole (D1)

A stirred mixture of 5-nitro-1H-indole (1.94 g, 12 mmole), 1-methylpiperidin-4-one (2.71 g, 24 mmole) and sodium methoxide (3.89 g, 72 mmole) in dry methanol (100 ml) was heated to reflux for 30 h. The cooled mixture was concentrated by evaporation and neutralized with 2M HCl acid. The resultant yellow precipitate was collected by filtration, washed with water and dried in vacuo to afford the title compound as a yellow powder (2.01 g).

$^1$H NMR (250 MHz, d$^6$DMSO) δ (ppm): 11.75 (s, 1H), 8.50 (s, 1H), 7.81 (dd, 1H), 7.52 (d, 1H), 7.38 (d, 1H), 5.91 (s, 1H), 2.72 (m, 4H), 2.41 (s, 3H) (NB—2H signals obscured by water signal).

DESCRIPTION 2

5-Amino-3-(1-methylpiperidin-4-yl)-1H-indole (D2)

A mixture of 3-(1-methyl-1,2,5,6-tetrahydropyridin-4-yl)-5-nitro-1H-indole (D1, 2.00 g, 7.8 mmole) and 10% palladium on carbon (0.25 g) in methanol (50 ml) and DMF (50 ml) was shaken under an atmosphere of hydrogen at 50 psi/344.8 KPa for 18 hours. The mixture was filtered and evaporated to dryness. The residue was partitioned between dichloromethane (75 ml) and water (30 ml). The organic phase was separated, washed with brine, dried (Na$_2$SO$_4$) and evaporated to dryness. Trituration of the residue with diethyl ether afforded the title compound as pale brown solid (1.15 g).

$^1$H NMR (250 MHz, CDCl$_3$) δ (ppm): 7.88 (s, 1H), 7.16 (d, 1H), 6.94 (d, 1H), 6.89 (d, 1H), 6.40 (dd, 1H), 3.49 (m, 2H), 2.95 (bd, 2H), 2.70 (m, 1H), 2.36 (s, 3H), 2.10 (m, 4H), 1.85 (m, 2H).

DESCRIPTION 3

4-(Pyridin-4-yl)naphth-1-ylamine (D3)

A stirred suspension of 4-bromonaphth-1-ylamine (10 g, 45 mmole) in 1,2-dimethoxyethane (400 ml) and water (100 ml) containing sodium carbonate (14 g) was flushed with argon for 0.3 hours. Tetrakis(triphenylphosphine) palladium (0) (2.75 g, 2.4 mmole) was added followed by pyridin-4-ylboronic acid (5.7 g, 46 mmole) and the mixture heated at reflux for 5 hours. The mixture was concentrated in vacuo to a brown slurry and partitioned between dichloromethane and water. The aqueous was further extracted with dichloromethane and the combined organics dried ($Na_2SO_4$) and concentrated in vacuo to a brown solid (13.2 g). Purification of the solid by flash chromatography eluting with ethyl acetate afforded the title compound as a yellow crystalline solid (7.8 g, 78%).

$^1$H NMR (250 MHz, $CDCl_3$) δ (ppm): 8.68 (d, 2H), 7.90 (d, 2H), 7.30 (m, 5H), 6.84 (d, 1H), 4.32 (s, 2H).

DESCRIPTION 4

1-Acetyl-7-(1-methyl-1,2,5,6-tetrahydropyridin-4-yl)-1,2,3,5-tetrahydropyrrolo [2,3-f]indole (D4)

To a stirred suspension of 1-acetyl-1,2,3,5-tetrahydropyrrolo[2,3-f]indole (J. Med. Chem. 1995, 38, 2524) (1.60 g, 8 mmole) and 1-methylpiperidin-4-one (1.81 g, 16 mmole) in dry methanol (70 ml) was added sodium methoxide (2.59 g, 48 mmole). The mixture was heated at reflux under argon for 24 hours, then cooled and concentrated by evaporation to approx. 25% volume; then treated with water (5 ml), stirred and the solid precipatate collected by filtration. The solid was suspended in ethanol (20 ml), heated to boiling, cooled and filtered to leave the title compound as a pale cream powder (1.20 g).

$^1$H HMR (250 MHz, $d^6$DMSO) δ (ppm): 11.03 (s, 1H), 8.61 (s, 1H), 7.32 (d, 1H), 7.23 (s, 1H), 6.03 (bs, 1H), 4.14 (t, 2H), 3.22 (t, 2H), 3.07 (d, 2H), 2.55 (m, 4H), 2.32 (s, 3H), 2.20 (s, 3H).

DESCRIPTION 5

1-Acetyl-7-(1-methylpiperidin-4-yl)-1,2,3,5-tetrahydropyrrolo[2,3-f]indole (D5)

A mixture of 1-acetyl-7-(1-methyl-1,2,5,6-tetrahydropyridin-4-yl)-1,2,3,5-tetrahydropyrrolo[2,3-f]indole (D4, 1.10 g, 3.7 mmole), 10% palladium on carbon (0.20 g) in MeOH (50 ml), DMF (10 ml) and glacial acetic acid (0.5 ml) was shaken under hydrogen at 50 psi/344.8 kPa for 42 hours. The mixture was filtered through Celite (Diatomaceous Earth) and the filtrate evaporated to dryness. The residue was dissolved in water (10 ml) and the pH adjusted to 8 with solid potassium carbonate. The precipitate was collected by filtration washed with water and dried in vacuo to leave the title compound as a buff powder (0.60 g).

$^1$H NMR (250 MHz, $d^6$DMSO) δ (ppm): 10.79 (s, 1H), 8.42 (s, 1H), 7.32 (s, 1H), 7.15 (s, 1H), 4.25 (t, 2H), 3.34 (t, 2H), 3.04 (br d, 2H), 2.80 (m, 1H), 2.37 (s, 3H), 2.32 (s, 3H), 2.22–2.02 (m, 4H), 1.90–1.72 (m, 2H).

DESCRIPTION 6

7-(1-Methylpiperidin-4-yl)-1,2,3,5-tetrahydropyrrolo [2,3-f]indole (D6)

To a stirred suspension of 1-acetyl-7-(1-methylpiperidin-4-yl)-1,2,3,5-tetrahydropyrrolo[2,3-f]indole (D5, 0.55 g, 1.85 mmole) in ethanol (10 ml) and 10% sodium hydroxide solution (10 ml) was added sodium hydroxide pellets (0.50 g) and the resultant mixture was heated at reflux under argon for 18 hours. The mixture was cooled, diluted with water (75 ml) and extracted with dichloromethane (5×30 ml). The combined organic extracts were washed with brine, dried ($MgSO_4$) and evaporated to dryness. The residue was triturated with diethyl ether and the solid filtered off and dried in vacuo to afford the title compound as an off-white powder (0.29 g).

$^1$H HMR (250 MHz, $d^6$DMSO) δ (ppm): 10.16 (s, 1H), 7.06 (s, 1H), 6.74 (d, 1H), 6.50 (s, 1H), 4.89 (s, 1H), 3.32 (m, 2H), 2.87–2.74 (m, 4H), 2.51 (m, 1H), 2.12 (s, 3H), 1.96–1.76 (m, 4H), 1.64–1.49 (m, 2H).

DESCRIPTION 7

4-(Pyridin-4-yl)naphth-1-ylacetic acid (D7)

4-Bromonaphth-1-ylacetic acid (J. Org. Chem., 1951, 16, 1588) (1 g, 3.78 mmole) in 1,2-dimethoxyethane (50 ml) was treated with pyridin-4-ylboronic acid (465 mg, 3.78 mmole), sodium hydrogen carbonate (952 mg, 11.3 mmole) and water (10 ml). A stream of argon was bubbled through the mixture for 15 minutes, then tetrakis (triphenylphosphine)palladium (0) (200 mg 0.17 mmole) was added and the mixture heated under reflux for 18 hours. The mixture was then concentrated in vacuo to a gum, which was partitioned between 2M sodium hydroxide solution and dichloromethane. The aqueous layer was separated, adjusted to pH 0 with 6M hydrochloric acid and washed with dichloromethane; then adjusted to pH 7 by addition of aqueous potassium carbonate solution and extracted with dichloromethane. The dichloromethane extract was dried ($Na_2SO_4$) and concentrated in vacuo to give the title compound, which crystallised from ether as needles mp 210–215° C. (465 mg, 46%).

$^1$H NMR (250 MHz, $CDCl_3$) δ (ppm): 8.55 (d, 2H), 8.0 (d, 1H), 7.7 (d, 1H), 7.5–7.3 (m, 5H), 7.2 (d, 1H), 6.1 (br s, 1H), 4.0 (s, 2H).

DESCRIPTION 8

N-[2,3-Dichloro-4-(pyridin-4-yl)phenyl]acetamide (D8)

The title compound was prepared from N-[4-bromo-2,3-dichlorophenyl]acetamide and pyridin-4-ylboronic acid using a similar procedure to Description 3.

$^1$H NMR (250 MHz, $d^6$DMSO) δ (ppm): 8.52 (d, 2H), 7.66 (d, 1H), 7.32 (d, 2H), 7.25 (d, 1H), 7.23 (br s, 1H), 1.98 (s, 3H).

DESCRIPTION 9

2,3-Dichloro-4-(pyridin-4-yl)aniline (D9)

A stirred suspension of N-[2,3-dichloro-4-(pyridin-4-yl) phenyl]acetamide (D8, 1 g, 3.6 mmole) in a mixture of 2M NaOH solution and ethanol (30 ml) was heated under reflux for 36 hours. The mixture was concentrated in vacuo and the residue extracted with dichloromethane. The extract was dried ($Na_2SO_4$) and concentrated in vacuo to afford the title compound as an orange solid (59%).

$^1$H NMR (250 MHz, $CDCl_3$) δ (ppm): 8.64 (d, 2H), 7.32 (d, 2H), 7.05 (d, 1H), 6.85 (d, 1H), 4.40 (br s, 2H).

DESCRIPTION 10

N-[2-Chloro-4-(pyridin-4-yl)phenyl]acetamide (D10)

The title compound was prepared from N-[4-bromo-2-chlorophenyl]acetamide and pyridin-4-ylboronic acid using a similar procedure to Description 3.

¹H HMR (250 MHz, CDCl₃) δ (ppm): 8.65 (d, 2H), 7.72 (br s, 1H), 7.68 (d, 1H), 7.58 (dd, 1H), 7.48 (d, 2H), 2.29 (s, 3H). NH not discernible from spectrum.

DESCRIPTION 11

2-Chloro-4-pyridin-4-yl)aniline (D11)

The title compound was prepared from N-[2-chloro-4-(pyridin-4-yl)phenyl]acetamide using a similar procedure to Description 9.

¹HNMR (250 MHz, CDCl₃) δ (ppm): 8.60 (d, 2H), 7.60 (d, 1H), 7.43 (d, 2H), 7.40 (dd, 1H), 6.87 (d, 1H), 4.30 (br s, 2H).

DESCRIPTION 12

5-Nitro-3-(pyridin-4-yl)benzo[b]thiophene (D12)

A stirred mixture of 3-bromo-5-nitrobenzo[b]thiophene (J.Amer. Chem. Soc, 1948, 1955) (4.2 g, 0.016 mole,) pyridin-4-ylboronic acid (2.0 g, 0.016 mole) and sodium carbonate (4.3 g, 0.048 mole) in DME (150 ml) and water (150 ml) was de-gassed by bubbling argon through for 15 minutes, then tetrakis(triphenylphosphine)palladium (0) (400 mg) was added and the mixture heated at reflux under argon for 18 hours. The reaction mixture was cooled and concentrated in vacuo to approx 150 ml volume, then acidified with 2M HCl acid (200 ml) and shaken well with ethyl acetate (400 ml). The solid present was filtered off, shaken with 10% Na₂CO₃ solution and dichloromethane, and the organic layer separated, dried (Na₂SO₄) and concentrated in vacuo to afford the title compound as an orange/yellow solid (2.3 g, 56%).

¹H NMR (250 MHz, CDCl₃) δ (ppm): 8.82–8.77 (m, 2H), 8.29 (dd, 1H), 8.07 (d, 1H), 7.77 (s, 1H), 7.52 (dd, 1H).

DESCRIPTION 13

3-(1-Methyl-1,2,5,6-tetrahydropyridin-4-yl)-5-nitrobenzo[b]thiophene (D13)

A solution of 5-nitro-3-(pyridin-4-yl)benzo[b]thiophene (D12, 1.5 g, 5.9 mmole) in chloroform (100 ml) was treated with iodomethane (0.55 ml, 8.8 mmole) and kept at room temperature for 11 days. The solid was filtered off, washed with chloroform and dried to afford the quaternary salt (2.11 g, 90%). This material was dissolved in a mixture of water (50 ml) and ethanol (50 ml) and treated portionwise over 10 minutes with sodium borohydride (0.50 g, 0.013 mole) at room temperature under argon. The reaction mixture was stirred for a further 2 hours, then concentrated under vacuum. The residue was treated with 10% Na₂CO₃ solution (50 ml) and extracted with dichloromethane. The extract was dried (Na₂SO₄), concentrated in vacuo and the residue purified by chromatography on basic alumina eluting with ethyl acetate to afford the title compound as a yellow solid (1.2 g, 83%).

¹H NMR (250 MHz, CDCl₃) δ (ppm): 8.82 (d, 1H), 8.19 (dd, 1H), 7.94 (d, 1H), 6.09 (quintet, 1H), 3.24–3.19 (m, 2H), 2.77–2.72 (m, 2H), 2.66–2.62 (m, 2H), 2.46 (s, 3H).

DESCRIPTION 14

5-Amino-3-(1-methyl-1,2,5,6-tetrahydropyridin-4-yl)benzo[b]thiophene (D14)

A stirred solution of 3-(1-methyl-1,2,5,6-tetrahydropyridin-4-yl)-5-nitrobenzo[b]thiophene (D13, 470 mg, 1.7 mmole) in ethanol (35 ml) at 60° C. under argon was treated over 5 minutes with a solution of tin (II) chloride (2.0 g, 10.5 mmole) in concentrated HCl acid (4 ml) and the mixture then heated at reflux for 1.5 hours. The reaction mixture was allowed to cool and the precipitate filtered off, washed with ethanol and dried. This was then shaken well with 10% Na₂CO₃ solution (50 ml) and dichloromethane (100 ml), and the organic layer separated, dried (Na₂SO₄) and concentrated in vacuo to afford the title compound as a yellow oil (310 mg, 75%).

¹H HMR (HCl salt) (250 MHz d⁶ DMSO) δ (ppm): 10.7 (s, 1H) 8.08 (d, 1H), 7.99 (d, 1H), 7.33 (dd, 1H), 6.04 (brs, 1H), 4.05–3.70 (m, 4H), 3.70–3.50 (m, 2H), 3.40–3.20 (m, 2H), 2.85 (s, 3H).

DESCRIPTION 15

5-Amino-3-(1-methylpiperidin-4-yl)benzo[b]thiophene (D15)

The title compound was prepared from 3-(1-methyl-1,2,5,6-tetrahydropyridin-4-yl)-5-nitrobenzo[b]thiophene (D13) using a similar procedure to Description 2 as a pink solid (72%).

¹H NMR (250 MHz, CDCl₃) δ (ppm): 7.61 (d, 1H), 7.06 (d+s, 2H), 6.78 (dd, 1H), 3.73 (br s, 2H), 3.05–2.95 (br d, 2H), 2.80 (tt, 1H), 2.35 (s, 3H), 2.20–2.02 (m, 2H), 1.96–174 (m, 4H).

EXAMPLE 1

N-[3-(1-Methylpiperdin-4-yl)indol-5-yl]-N'-[4-(pyridin-4-yl)naphth-1-yl]-urea (E1)

To a stirred solution of triphosgene (0.09 g, 0.31 mmole) in dichloromethane (15 ml) under argon, was added dropwise a solution of 4-(pyridin-4-yl)naphth-1-ylamine (D3, 0.17 g, 0.77 mmole) and triethylamine (0.12 ml, 0.83 mmole) in dichloromethane (10 ml). The mixture was then stirred at room temperature for 20 minutes, then a solution of 5-amino-3-(1-methylpiperidin-4-yl)-1H-indole (D2, 0.15 g, 0.66 mmole) in dichloromethane (10 ml) was slowly added. After stirring the mixture for 1 hour, dilute potassium carbonate solution (10 ml) was added. The precipitated solid mass was collected and purified by flash chromatography on silica gel eluting with CH₂Cl₂/MeOH/NH₄OH (100:10:1) to afford the title compound as a buff powder (0.14 g).

¹H NMR (250 MHz, d⁶DMSO) δ (ppm): 10.72 (s, 1H), 9.02 (s, 1H), 8.87 (s, 1H), 8.72 (d, 2H), 8.29 (d, 1H), 8.24 (d, 1H), 7.86 (m, 2H), 7.71–7.48 (m, 5H), 7.32 (d, 1H), 7.14 (d, 1H), 7.08 (s, 1H), 2.95 (d, 2H), 2.72 (m, 1H), 2.27 (s, 3H), 2.18 (m, 2H), 1.96 (m, 2H), 1.78 (m, 2H).

EXAMPLE 2

N-[3-(1-Methylpiperidin-4-yl)indol-5-yl]-N'-[3-methyl-4-(pyridin-4-yl)phenyl]-urea (E2)

The title compound was prepared in a similar manner to Example 1 from 3-methyl-4-(pyridin-4-yl)aniline (prepared as for D3 from 4-bromo-3-methylaniline) (0.17 g, 0.9 mmole), 5-amino-3-(1-methylpiperdin-4-yl)-1H-indole (D2, 0.17 g, 0.75 mmole), triphosgene (0.10 g, 0.35 mmole) and triethylamine (0.07 ml). This was obtained as a buff powder (0.11 g).

¹H HMR (250 MHz, d⁶DMSO) δ (ppm): 10.64 (s, 1H), 8.62 (s, 1H), 8.57 (d, 2H), 8.47 (s, 1H), 7.73 (s, 1H), 7.37 (m, 4H), 7.24–6.98 (m, 4H), 2.87 (m, 2H), 2.63 (m, 1H), 2.26 (s, 3H), 2.19 (s, 3H), 2.05–1.85 (m, 4H), 1.70 (m, 2H).

EXAMPLE 3

N-[2,3-Dichloro-4-(pyridin-4-yl)phenyl]-N'-[3-(1-methylpiperidin-4-yl)indol-5-yl]-urea (E3)

The title compound was prepared in a similar manner to Example 1 from 2,3-dichloro-4-(pyridin-4-yl)aniline (D9, 0.20 g, 0.85 mmole), 5-amino-3-(1-methylpiperidin-4-yl)-1H-indole (D2, 0.15 g, 0.66 mmole), triphosgene (0.10 g, 0.34 mmole) and triethylamine (0.30 ml). This was obtained as a pink white solid (0.18 g).

$^1$HNMR (250 MHz, d$^6$DMSO) δ (ppm): 10.68 (s, 1H), 9.39 (s, 1H), 8.50 (d, 2H), 8.45 (s, 1H), 8.20 (d, 1H), 7.68 (s, 1H), 7.31 (d, 2H), 7.25 (d, 1H), 7.12 (d, 1H), 6.96 (s, 1H), 6.83 (d, 1H), 3.30 (m, 1H), 2.97 (m, 2H), 2.72 (s, 3H), 1.98–1.78 (m, 6H).

EXAMPLE 4

N-[2-Chloro-4-(pyridin-4-yl)phenyl]-N'-[3-(1-methylpiperidin-4-yl)indol-5-yl]-urea (E4)

The title compound was prepared in a similar manner to Example 1 from 2-chloro-4-(pyridin-4-yl)aniline (D11, 0.18 g, 0.88 mmole), 5-amino-3-(1-methylpiperidin-4-yl)-1H-indole (D2, 0.15 g, 0.66 mmole), triphosgene (0.10 g, 0.34 mmole) and triethylamine (0.3 ml). This was obtained as a pink-white solid (0.20 g).

$^1$H NMR (250 MHz, d$^6$DMSO) δ (ppm): 10.66 (s, 1H), 9.34 (s, 1H), 8.40 (d, 2H), 8.32 (s, 1H), 8.22 (d, 1H), 7.76 (d, 1H), 7.64–7.53 (m, 4H), 7.12 (d, 1H), 6.93 (s, 1H), 6.82 (d, 1H), 3.24 (m, 1H), 2.94 (m, 2H), 2.57 (s, 3H), 1.97–1.77 (m, 6H).

EXAMPLE 5

N-[3-(1-Methylpiperidin-4-yl)indol-5-yl]-4-(pyridin-4-yl)naphth-1-ylacetamide (E5)

A stirred suspension of 4-(pyridin-4-yl)naphth-1-ylacetic acid (D7, 0.18 g, 0.7 mmole) in dichloromethane (15 ml) was treated with oxalyl chloride (0.18 ml, 2.1 mmoles), then stirred at room temperature for 3 hours, before evaporating to dryness. The solid residue was suspended in dichloromethane (15 ml), cooled to 0° C. and treated with a solution of 5-amino-3-(1-methylpiperidin-4-yl)-1H-indole (D2, 0.13 g, 0.56 mmole) in dichloromethane (15 ml). The mixture was stirred at 0° for 1 hour and then a solution of triethylamine (0.25 ml) in dichloromethane (5 ml) was added dropwise. The mixture was allowed to warm to room temperature and stir overnight, then evaporated to dryness and the residue subjected to flash chromatography on silica gel eluting with CH$_2$Cl$_2$/MeOH/NH$_4$OH (100:5:0.5 to 100:10:1 gradient elution) to afford the title compound as a pale cream powder (0.04 g).

$^1$H HMR (250 MHz, CDCl$_3$) δ (ppm): 8.75 (d, 2H), 8.20 (d, 1H), 8.05 (s, 1H), 7.91 (d, 1H), 7.76 (s, 1H), 7.62–7.43 (m, 6H), 7.22 (m, 2H), 6.97 (m, 1H), 4.26 (s, 2H), 2.97 (d, 2H), 2.73 (m, 1H), 2.32 (s, 3H), 2.13–1.95 (m, 4H), 1.77 (m, 2H).

EXAMPLE 6

N-[2,3-Dichlorophenyl]-N'-[7-(1-methylpiperidin-4-yl)-1,2,3,5-tetrahydropyrrolo[2,3-f]indol-1-yl]-urea (E6)

To a stirred solution of 7-(1-methylpiperidin-4-yl)-1,2,3,5-tetrahydropyrrolo[2,3-f]indole (D6, 0.10 g, 0.4 mmole) in dichloromethane (10 ml) was added dropwise a solution of 2,3-dichlorophenylisocyanate (0.08 g, 0.44 mmole) in dichloromethane (10 ml). The mixture was stirred at room temperature overnight, then concentrated by evaporation and diethyl ether (10 ml) added. The precipitated solid was collected by filtration, washed with diethyl ether and dried in vacuo to afford the title compound as a colourless powder (0.12 g).

$^1$H HMR (250 MHz, d$^6$DMSO) δ (ppm): 10.49 (s, 1H), 8.21 (s, 1H), 7.92 (s, 1H), 7.64 (d, 1H), 7.40–7.25 (m, 2H), 7.08 (s, 1H), 6.88 (d, 1H), 4.08 (t, 2H), 3.15 (t, 2H), 2.78 (d, 2H), 2.50 (m, 1H), 2.10 (s, 3H), 1.95–1.75 (m, 4H), 1.65–1.57 (m, 2H).

EXAMPLE 7

N-[7-(1-Methylpiperidin-4-yl)-1,2,3,5-tetrahydropyrrolo[2,3-f]indol-1-yl]-N'-[-4-(pyridin-4-yl)naphth-1-yl]-urea (E7)

The title compound was prepared in a similar manner to Example 1 from 4-(pyridin-4-yl)naphth-1-ylamine (D3, 0.16 g, 0.7 mmole), 7-(1-methylpiperidin-4-yl)-1,2,3,5-tetrahydropyrrolo[2,3-f]indole (D6, 0.15 g, 0.6 mmole), triphosgene (0.08 g, 0.28 mmole) and triethylamine (0.25 ml). This was obtained as a cream powder (0.11 g).

$^1$H NMR (250 MHz, d$^6$DMSO) δ (ppm): 10.64 (s, 1H), 8.90 (dd, 3H), 8.35 (dd, 1H), 8.20 (s, 1H), 7.95 (dd, 1H), 7.83 (d, 1H), 7.80–7.62 (m, 5H), 7.34 (s, 1H), 7.12 (d, 1H), 4.50 (t, 2H), 3.45 (t, 2H), 2.95 (d, 2H), 2.77 (m, 1H), 2.32 (s, 3H), 2.17–2.04 (m, 4H), 1.88–1.76 (m, 2H).

EXAMPLE 8

N-[3-Chloro-4-(pyridin-4-yl)phenyl]-N'-[3-(1-methylpiperidin-4-yl)indol-5-yl]-3-urea (E8)

The title compound was prepared in a similar manner to Example 1 from 3-chloro-4-(pyridin-4-yl)aniline (prepared using a similar procedure to Description 11) (0.18 g, 0.88 mmole), 5-amino-3-(1-methylpiperidin-4-yl)-1H-indole (D2, 0.15 g, 0.66 mmole), triphosgene (0.10 g, 0.34 mmole) and triethylamine (0.3 ml). This was obtained as a off-white powder.

$^1$H HMR (250 MHz, d$^6$DMSO) δ (ppm): 10.54 (s, 1H), 8.92 (s, 1H), 8.54 (s, 1H), 8.49 (d, 2H), 7.75 (s, 1H), 7.60 (s, 1H), 7.34 (d, 2H), 7.28 (m, 2H), 7.09 (d, 1H), 6,91 (m, 2H), 2.76 (d, 2H), 2.52 (m, 1H), 2.08 (s, 3H)

EXAMPLE 9

N-[3-Chloro-4-(pyridin-4-yl)phenyl]-N'-[3-(1-methyl-1,2,5,6-tetrahydropyridin-4-yl)benzo[b]thiophen-5-yl]-urea (E9)

The title compound was prepared from 3-chloro-4-(pyridin-4-yl)aniline (prepared using a similar procedure to Description 11) and 5-amino-3-(1-methyl-1,2,5,6-tetrahydropyridin-4-yl)benzo[b]thiophene (D14) using a similar procedure to Example 1 as a beige solid (41%).

$^1$H NMR (250 MHz CDCl$_3$) δ (ppm): 8.57 (d, 2H), 8.36 (s, 1H), 8.18 (s, 1H), 7.98 (s, 1H), 7.56 (d, 1H), 7.42 (s, 1H), 7.30–7.12 (m, 3H), 7.09 (d, 1H), 7.00 (d, 1H), 5.90 (br s, 1H), 3.02 (br s, 2H), 2.65–2.45 (m, 4H), 2.34 (s, 3H).

EXAMPLE 10

N-[3-(1-Methyl-1,2,5,6-tetrahydropyridin-4-yl)benzo[b]thiophen-5-yl]-N'-[4-(pyridin-4-yl)naphth-1-yl]-urea (E10)

The title compound was prepared from 4-(pyridin-4-yl)naphth-1-ylamine (D3) and 5-amino-3-(1-methyl-1,2,5,6- tetrahydropyridin-4-yl)benzo[b]thiophene (D14) using a similar procedure to Example 1 as a beige solid (48%).

$^1$H NMR (250 MHz, CDCl$_3$) δ (ppm): 8.69–8.64 (m, 2H), 8.00–7.95 (m, 2H), 7.80–7.72 (m, 4H), 7.55 (d, 1H), 7.44–7.17 (m, 7H), 5.91 (br s, 1H), 3.03–2.96 (m, 2H), (m, 4H), 2.32 (s, 3H)

EXAMPLE 11

N-[3-Chloro-4-(pyridin-4-yl)phenyl]-N'-[3-(1-methylpiperidin-4-yl)benzo[b]thiophen-5-yl]-urea (E11)

The title compound was prepared from 3-chloro-4-(pyridin-4-yl)aniline (D11) and 5-amino-3-(1-methylpiperidin-4-yl)benzo[b]thiophene (D15) using a similar procedure to Example 1 as a white solid (41%).

$^1$H NMR (250 MHz, CDCl$_3$) δ (ppm): 8.60–8.55 (m, 2H), 8.25 (brs, 1H), 8.20 (brs, 1H), 8.00 (d, 1H), 7.75 (d, 1H), 7.70 (d, 1H), 7.47 (dd, 1H), 7.42–7.33 (m, 3H), 7.23 (d, 1H), 7.17 (s, 1H), 3.07–2.80 (m, 3H), 2.36 (s, 3H), 2.29–2.15 (m, 2H), 2.04–1.90 (m, 4H).

EXAMPLE 12

N-[3-(1-Methylpiperidin-4-yl)benzo[b]thiophen-5-yl]-N'-[-4-(pyridin-4-yl)naphth-1-yl]-urea (E12)

The title compound was prepared from 4-(pyridin-4-yl)naphth-1-ylamine (D3) and 5-amino-3-(1-methylpiperidin-4-yl)benzo[b]thiophene (D15) using a similar procedure to Example 1 (E1) as a white solid (43%).

$^1$H NMR (250 MHz, CDCl$_3$) δ (ppm): 8.73–8.67 (m, 2H), 8.05–7.97 (m, 2H), 7.86–7.77 (m, 2H), 7.66 (d, 1H), 7.50–7.28 (m, 7H), 7.14–7.05 (m, 2H), 3.00–2.75 (m, 3H), 2.28 (s, 3H), 2.10–1.80 (m, 6H).

Pharmacological Data

The affinities of the compounds of this invention were determined by methods described above.

5-HT$_{1A}$, 5-HT$_{1B}$ and 5-HT$_{1D}$ Receptor Binding

Examples 1, 3, 4, 8, 9, 10 and 12 had pKi values>8.0 at 5-HT$_{1A}$, 5-HT$_{1B}$ and 5-HT$_{1D}$ receptors.

What is claimed is:

1. A compound of formula (I) or a salt thereof:

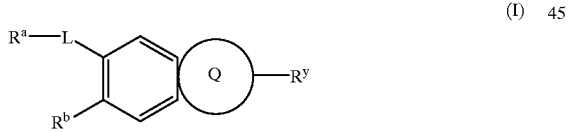

(I)

in which $R^a$ is a group of formula (i)

(i)

in which $P^1$ is phenyl, bicyclic aryl, a 5 to 7 membered heterocyclic ring containing 1 to 3 heteroatoms selected from oxygen, nitrogen and sulphur, or a bicyclic heterocyclic ring containing 1 to 3 heteroatoms selected from oxygen, nitrogen and sulphur;

$R^1$ is hydrogen, halogen, $C_{1-6}$alkyl, $C_{3-6}$cycloalkyl, $COC_{1-6}$alkyl, $C_{1-6}$alkoxy, hydroxy, hydroxy$C_{1-6}$alkyl, hydroxy$C_{1-6}$alkoxy, $C_{1-6}$alkoxy$C_{1-6}$alkoxy, nitro, trifluoromethyl, cyano, $SR^9$, $SOR^9$, $SO_2R^9$, $SO_2NR^{10}R^{11}$, $CO_2R^{10}$, $CONR^{10}R^{11}$, $CONR^{10}(CH_2)_cCO_2R^{11}$, $(CH_2)_cNR^{10}R^{11}$, $(CH_2)_cCONR^{10}R^{11}$, $(CH_2)_cNR^{10}COR^{11}$, $(CH_2)_cCO_2C_{1-6}$alkyl, $CO_2(CH_2)_cOR^{10}$, $NR^{10}R^{11}$, $NR^{10}CO_2R^{11}$, $NR^{10}CONR^{10}R^{11}$, $CR^{10}=NOR^{11}$ where $R^9$ is $C_{1-6}$alkyl, $R^{10}$ and $R^{11}$ are independently hydrogen or $C_{1-6}$alkyl and c is 1 to 4;

$R^2$ is hydrogen, halogen, $C_{1-6}$alkyl, $C_{3-6}$cycloalkyl, $C_{3-6}$cycloalkenyl, $C_{1-6}$alkoxy, $COC_{1-6}$alkyl, aryl, acyloxy, hydroxy, nitro, trifluoromethyl, cyano, $CO_2R^{10}$, $CONR^{10}R^{11}$, $NR^{10}R^{11}$ where $R^{10}$ and $R^{11}$ are as defined for $R^1$;

a is 1,2 or 3;

or $R^a$ is a group of formula (ii)

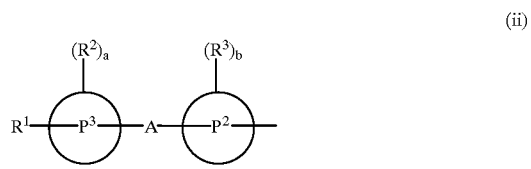

(ii)

wherein $P^2$ and $P^3$ are independently phenyl, bicyclic aryl, a 5- to 7-membered heterocyclic ring containing 1 to 3 heteroatoms selected from oxygen, nitrogen and sulphur, or a bicyclic heterocyclic group containing 1 to 3 heteroatoms selected from oxygen, nitrogen or sulphur; A is a bond or oxygen, $S(O)_m$ where m is 0, 1 or 2, carbonyl, or $CH_2$ or $NR^4$ where $R^4$ is hydrogen or $C_{1-6}$alkyl;

$R^1$ is as defined above for formula (i) or is a 5 to 7-membered heterocyclic ring, containing 1 to 3 heteroatoms selected from oxygen, nitrogen or sulphur, optionally substituted by $C_{1-6}$alkyl, halogen or $C_{1-6}$alkanoyl;

$R^2$ and $R^3$ are as defined for $R^2$ in formula (i);

and a and b are independently 1, 2 or 3;

L is a group of formula

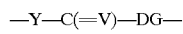

—Y—C(=V)—DG— in which Y is —NH—,;

V is oxygen or sulphur;

D is nitrogen;

G is hydrogen or $C_{1-6}$alkyl;

Q is thienyl;

$R^y$ is a 5- to 7-membered heterocyclic ring containing 1 to 3 heteroatoms selected from oxygen, nitrogen and sulphur;

$R^b$ is hydrogen, halogen, hydroxy, $C_{1-6}$alkyl, trifluoromethyl, $C_{1-6}$alkoxy or aryl;

2. A compound according to claim 1 in which $R^2$ and/or $R^3$ are each hydrogen, halogen or a $C_{1-6}$alkyl group.

3. A compound according to claim 1 in which G is a hydrogen atom.

4. A compound according to claim 1 which is:
N-[3-chloro-4-(pyridin-4-yl)phenyl]-N'-[3-(1-methyl-1,2,5,6-tetrahydropyridin-4-yl)benzo[b]thiophen-5-yl]-urea,
N-[3-(1-methyl-1,2,5,6-tetrahydropyridin-4-yl)benzo[b]thiophen-5-yl]-N'-[4-(pyridin-4-yl)naphth-1-yl]-urea,
N-[3-chloro-4-(pyridin-4-yl)phenyl]-N'-[3-(1-methylpiperidin-4-yl)benzo[b]thiophen-5-yl]-urea, and
N-[3-(1-methylpiperidin-4-yl)benzo[b]thiophen-5-yl]-N'-[4-(pyridin-4-yl)naphth-1-yl]-urea;
or a pharmaceutically acceptable salt thereof.

5. A pharmaceutical composition which comprises a therapeutic effective amount of a compound according to claim 1 and a pharmaceutically acceptable carrier.

6. A method for treating anxiety and/or depression which method comprises administering to a patient in need thereof an effective amount of a compound of formula (I) according to claim 1 either alone or in combination with a pharmaceutically acceptable excipient.

* * * * *